United States Patent
Gunn et al.

(10) Patent No.: US 9,044,274 B2
(45) Date of Patent: Jun. 2, 2015

(54) BONE SCREW SYSTEM

(75) Inventors: Joshua D. Gunn, Marietta, GA (US);
Jeffrey S. Radcliffe, Marietta, GA (US);
Mark W. Jacob, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 776 days.

(21) Appl. No.: 12/957,965

(22) Filed: Dec. 1, 2010

(65) Prior Publication Data
US 2012/0143260 A1    Jun. 7, 2012

(51) Int. Cl.
*A61B 17/70* (2006.01)

(52) U.S. Cl.
CPC .................................. *A61B 17/7037* (2013.01)

(58) Field of Classification Search
CPC .......................... A61B 17/7035; A61B 17/7037
USPC .................. 606/264–272, 300–305, 319, 322
See application file for complete search history.

(56) References Cited

U.S. PATENT DOCUMENTS

| | | | |
|---|---|---|---|
| 5,256,149 A | 10/1993 | Banik | |
| 5,601,554 A | 2/1997 | Howland | |
| 5,782,833 A * | 7/1998 | Haider | 606/266 |
| 5,954,725 A * | 9/1999 | Sherman et al. | 606/78 |
| 6,203,559 B1 | 3/2001 | Davis | |
| 6,743,231 B1 | 6/2004 | Gray | |
| 7,056,321 B2 | 6/2006 | Pagliuca | |
| 7,163,539 B2 | 1/2007 | Abdelgany | |
| 7,494,489 B2 | 2/2009 | Roh | |
| 7,588,575 B2 | 9/2009 | Colleran | |
| 7,618,442 B2 | 11/2009 | Spitler | |
| 7,648,520 B2 | 1/2010 | Markworth | |
| 7,651,496 B2 | 1/2010 | Keegan | |
| 7,678,139 B2 | 3/2010 | Garamszegi | |
| 2004/0215190 A1 * | 10/2004 | Nguyen et al. | 606/61 |
| 2005/0090833 A1 | 4/2005 | DiPoto | |
| 2005/0187548 A1 | 8/2005 | Butler | |
| 2005/0261687 A1 | 11/2005 | Garamszegi et al. | |
| 2005/0283157 A1 * | 12/2005 | Coates et al. | 606/73 |
| 2006/0064089 A1 * | 3/2006 | Jackson | 606/61 |
| 2006/0195017 A1 | 8/2006 | Shluzas | |
| 2006/0229615 A1 | 10/2006 | Abdou | |
| 2007/0021750 A1 | 1/2007 | Shluzas | |
| 2007/0043358 A1 * | 2/2007 | Molz et al. | 606/61 |
| 2007/0043364 A1 * | 2/2007 | Cawley et al. | 606/61 |
| 2007/0066987 A1 | 3/2007 | Scanlan | |
| 2007/0090238 A1 | 4/2007 | Justis | |
| 2007/0161991 A1 | 7/2007 | Altarac | |
| 2007/0233079 A1 | 10/2007 | Fallin | |
| 2007/0288003 A1 | 12/2007 | Dewey | |
| 2008/0045953 A1 | 2/2008 | Garamszegi | |
| 2008/0177321 A1 * | 7/2008 | Drewry et al. | 606/266 |
| 2008/0188895 A1 | 8/2008 | Cragg | |
| 2008/0262551 A1 | 10/2008 | Rice | |
| 2009/0099605 A1 | 4/2009 | Fallin | |
| 2009/0149887 A1 | 6/2009 | Schlapfer et al. | |

(Continued)

OTHER PUBLICATIONS

The International Search Report and Written Opinion issued on Dec. 16, 2011 in PCT/US2011/047704.

*Primary Examiner* — Jan Christopher Merene
*Assistant Examiner* — Atiya Mahmud
(74) *Attorney, Agent, or Firm* — David L. King

(57) ABSTRACT

A bone screw system is presented. The bone screw system has a fixation element, a receiving element, coupling element, and a compression element. In one aspect, the fixation element is adapted to engage a bone and has a head portion and a threaded shank portion.

10 Claims, 9 Drawing Sheets

(56) References Cited

U.S. PATENT DOCUMENTS

2009/0216278 A1 8/2009 Song
2009/0270916 A1 10/2009 Ramsay
2010/0228293 A1 9/2010 Courtney et al.
2010/0324599 A1* 12/2010 Montello et al. .............. 606/264
2011/0160779 A1* 6/2011 Schlaepfer et al. ........... 606/305

* cited by examiner

BONE SCREW SYSTEM

FIELD OF THE INVENTION

Presented herein is a bone screw system. More specifically, a bone screw for use in spinal surgery is presented.

BACKGROUND OF THE INVENTION

Spinal surgeons often treat spinal disorders with spinal fusion augmented with elongated spinal rods connected to the spine with pedicle screws. Such "rod assemblies" generally comprise one or two spinal rods and a plurality of screws inserted through the pedicles and into their respective vertebral bodies. The screws are provided with connectors, for coupling the spinal rods to the screws. The spinal rods extend along the longitudinal axis of the spine, coupling to the plurality of screws via their connectors. The aligning influence of the rods forces the patient's spine to conform to a more appropriate shape.

SUMMARY

Presented herein is a bone screw system that comprises a fixation element, a receiving element, coupling element, and a compression element. In one aspect, the fixation element is adapted to engage a bone and has a head portion and a threaded shank portion. The receiving element is configured for receipt of the head portion of the fixation element and has a channel to receive a stabilizer bar. The coupling element, positioned below the stabilizer bar when it is in position, couples to the head portion of the fixation element and is configured to translate force from the stabilizer bar to the head portion of the fixation element to substantially press the head portion against the seat of the receiving element. The compression element, which is positionable within a portion of the receiving element, is configured to apply a force to the stabilizer bar, which is then transferred to the coupling element.

Other aspects and embodiments of the bone screw system are described herein. This description is meant to fully describe the bone screw system, but not limit its design, function, or application.

BRIEF DESCRIPTION OF THE DRAWINGS

These and other features of the preferred embodiments of the present invention will become more apparent in the detailed description in which reference is made to the appended drawings wherein.

DETAILED DESCRIPTION OF THE INVENTION

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a screw" can include two or more such screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 9:
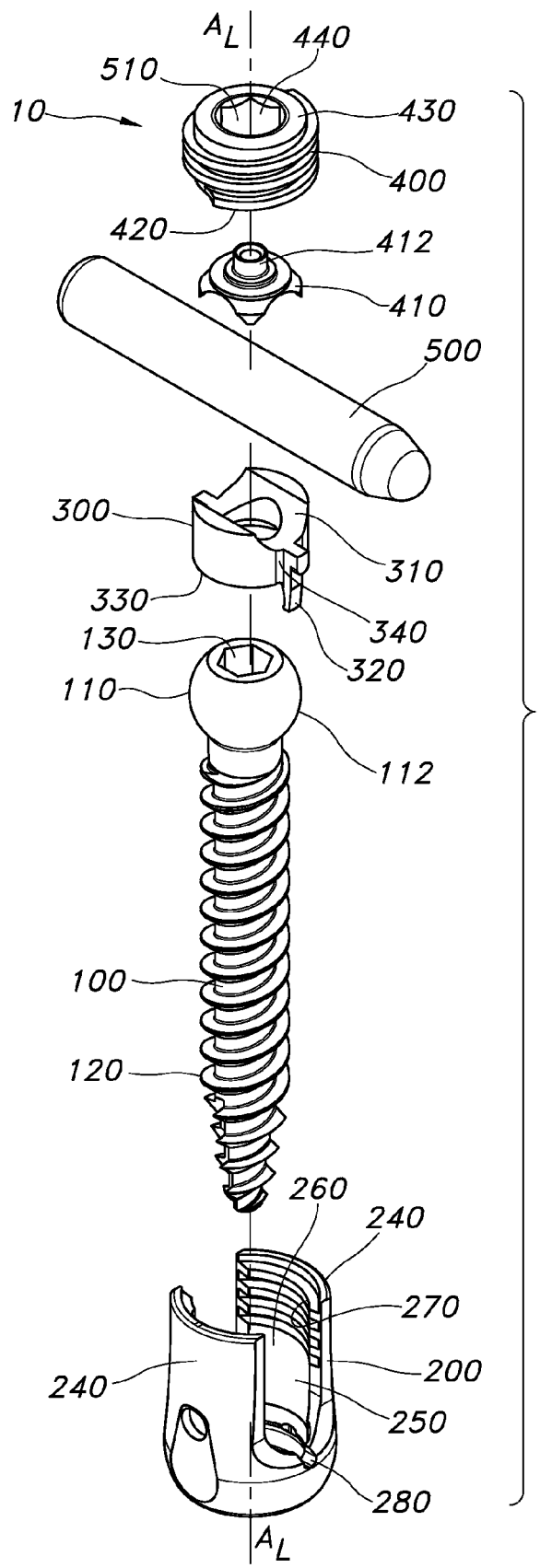
FIG. 9 is an exploded front perspective view of the bone screw system of FIG. 1.

Presented herein is a bone screw system 10 that comprises a fixation element 100, a receiving element 200, coupling element 300, and a compression element 400. In one aspect, the fixation element 100 is adapted to engage a bone and has a head portion 110 and a threaded shank portion 120. The fixation element can be a screw. In an exemplified aspect, the head portion is substantially spherical, or substantially semispherical, although other shapes are contemplated. As one skilled in the art can appreciate, the fixation element can comprise a pedicle screw, such as a standard fast-pitch, double-lead pedicle screw. As such, the head portion 110 can be configured to engage the particular insertion tool designed for the system 10. In one aspect, the head portion of the fixation element defines a screw tool bore 130 configured for engagement with the insertion tool. As illustrated in FIG. 9, the screw tool bore 130 can be a hex shaped bore or other shape that mates with a corresponding insertion tool or driver.

Figure 1:
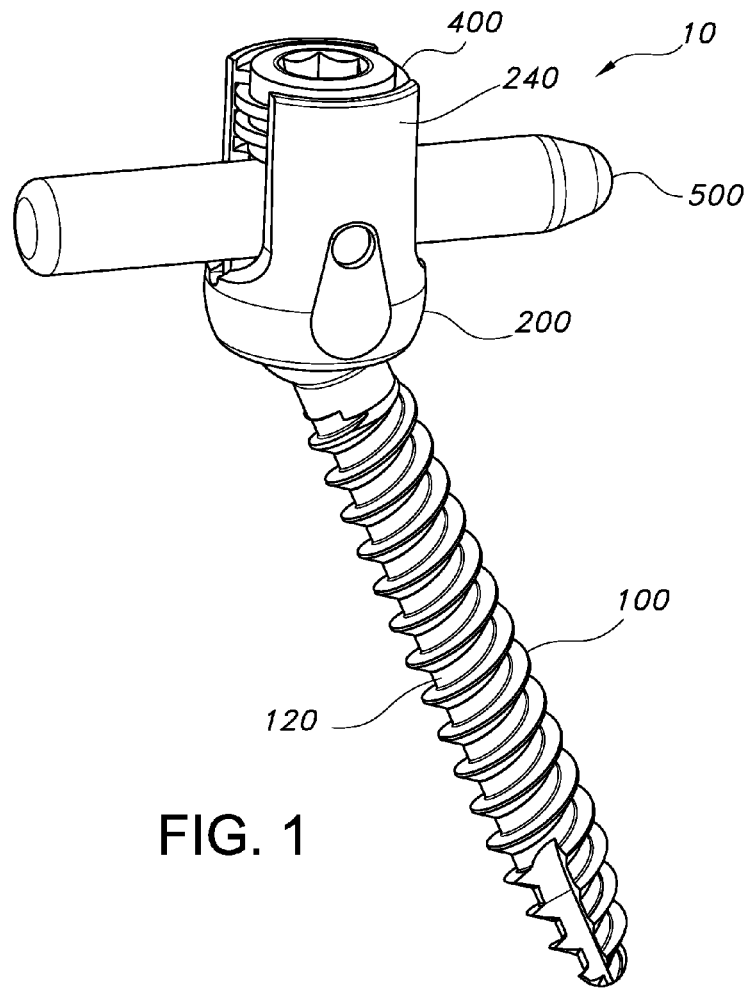
FIG. 1 is a perspective view of one aspect of a bone screw system.
Figure 2:
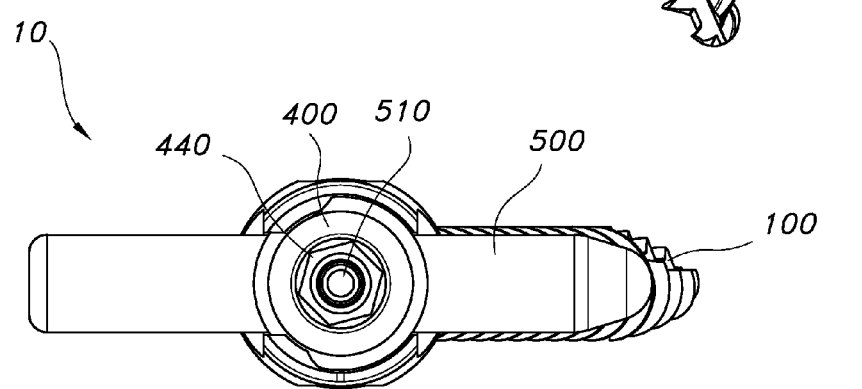
FIG. 2 is a top plan view of the bone screw system of FIG. 1, showing a portion of the stabilizer bar.
Figures 3, 4:
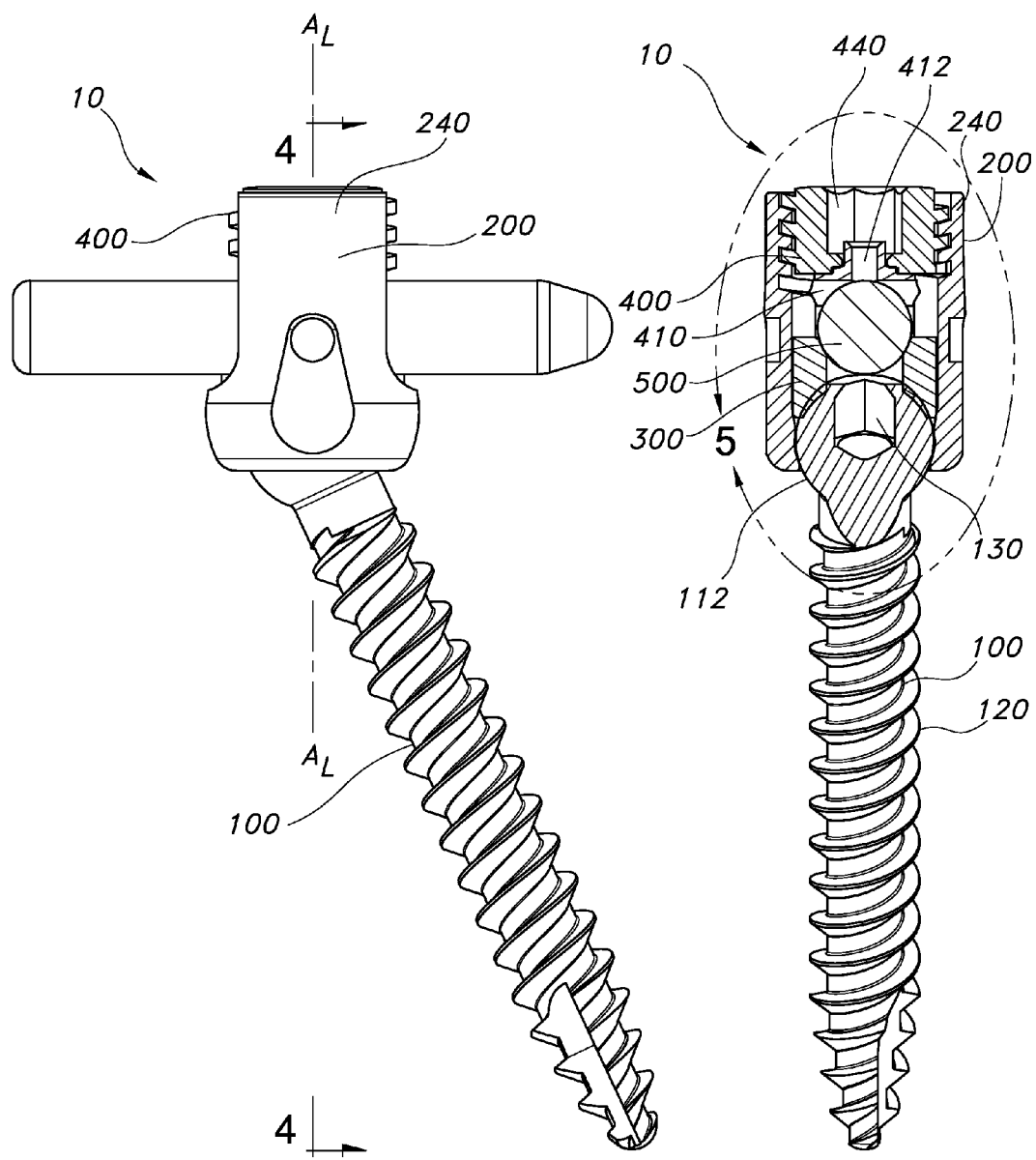
FIG. 3 is a front elevational view of the bone screw system of FIG. 1.
FIG. 4 is a cut-away right side elevation view of the bone screw system of FIG. 1, cut along line 4-4 of FIG. 3.
Figure 5:
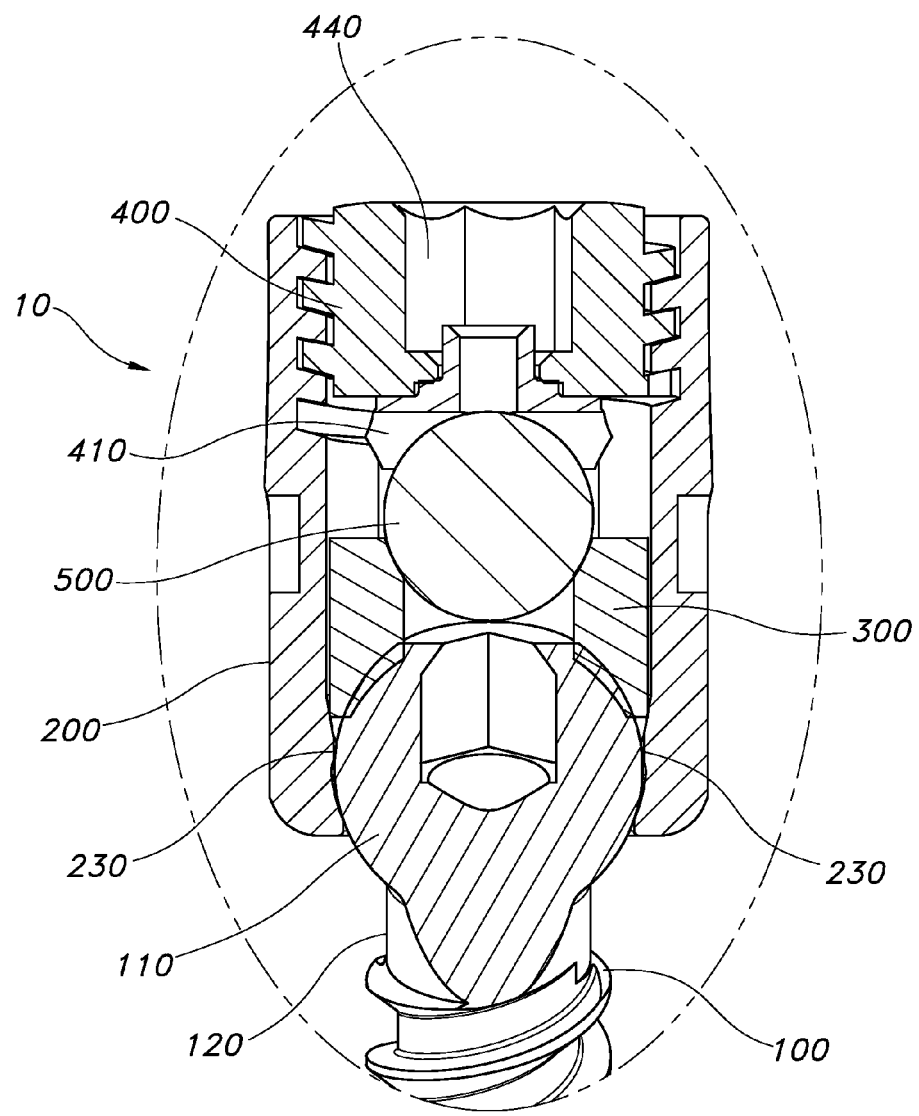
FIG. 5 is an exploded cut-away front elevational view of Section 5 of FIG. 4 of the bone screw system of FIG. 1
Figures 6, 7:
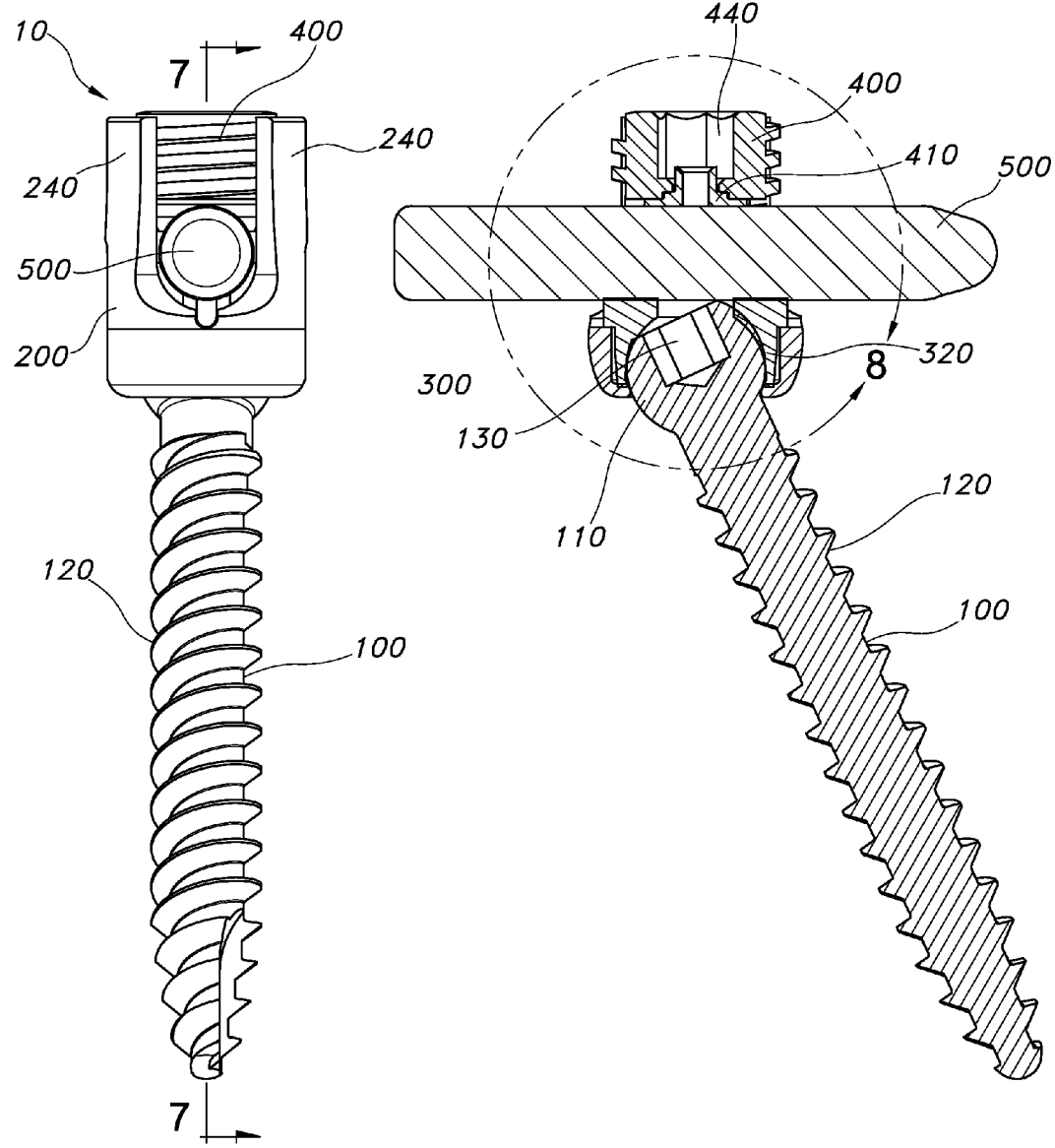
FIG. 6 is a right side elevational view of the bone screw system of FIG. 1.
FIG. 7 a cut-away front elevational view of the bone screw system of FIG. 1, cut along line 7-7 of FIG. 6.
Figure 8:
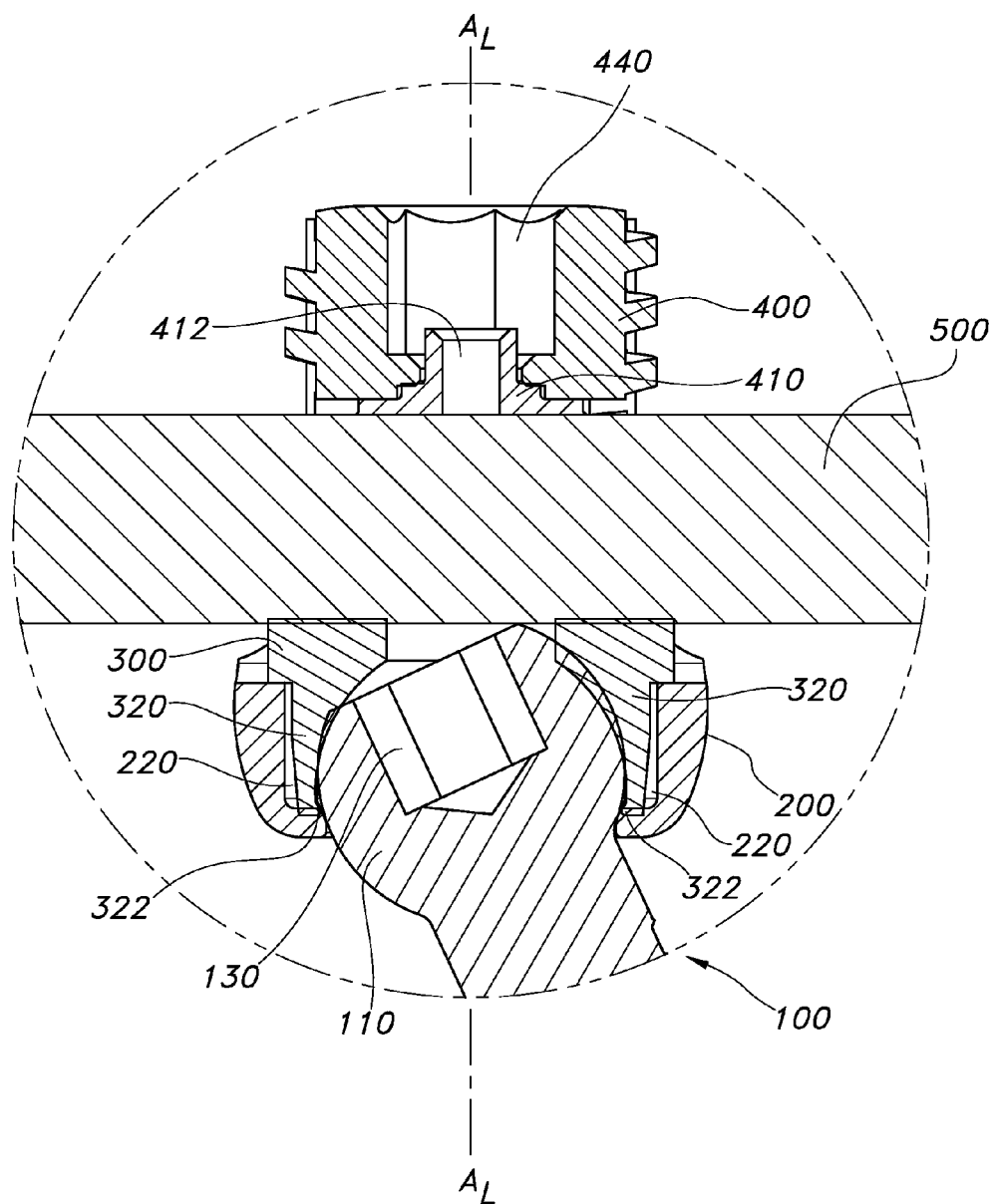
FIG. 8 is an exploded cut-away front elevational view of Section 8 of FIG. 7 of the bone screw system of FIG. 1.
Figure 11:
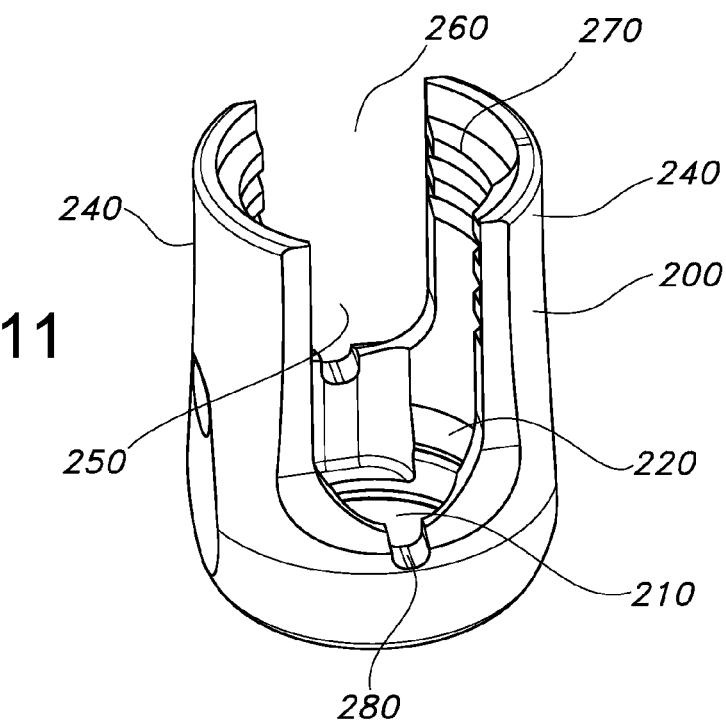
FIG. 11 is a perspective view of one aspect of a receiving element for use in a bone screw system.
Figure 12:
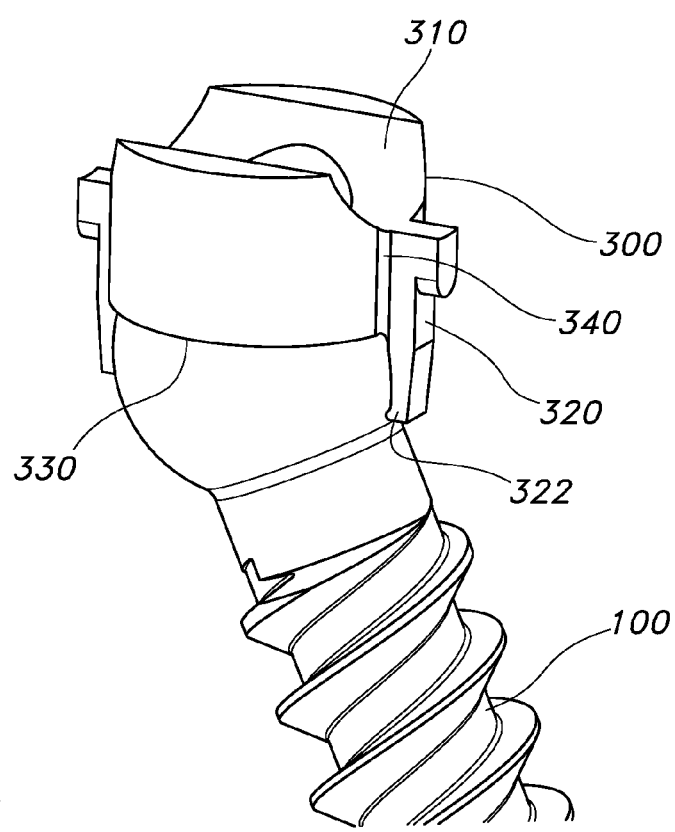
FIG. 12 is a perspective view of one aspect of a coupling element coupled thereto a head portion of a fixation element of for use with a bone screw system.
Figure 13:
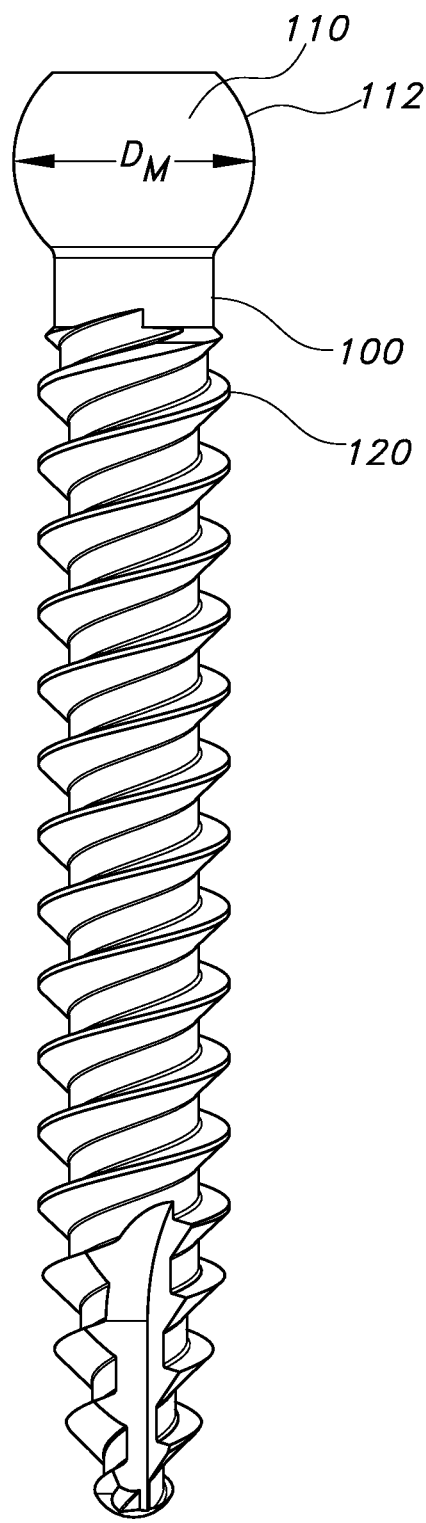
FIG. 13 is a side elevational view of one aspect of a fixation element for use with a bone screw system.

The receiving element 200, as illustrated in FIG. 11, defines an internal bore 210 sized to receive the shank portion 120 of the fixation element 100 and a seat 220 adapted to support the head portion of the fixation element. The seat 220 of the receiving element is shaped to substantially conform to an exterior portion 112 of the head portion of the fixation element. In one aspect, the receiving element is adapted to retain the head portion 110 of the fixation element within the receiving element while substantially permitting rotational movement of the fixation element 100 with respect to the receiving element 200. In one exemplified aspect, the fixation element is permitted to move polyaxially with respect to the receiving element, but cannot substantially move up and down. To accomplish this, in one aspect, as shown in FIG. 5, the receiving element further defines at least two opposed pinch points 230 configured as projections formed that are spaced less than a maximum diameter DM of the head portion of the fixation element. These pinch points 230 can be biased away from each other by compressing the head portion of the fixation element into the seat such that, as the portion of the head portion with the maximum diameter DM passes the pinch points, the pinch points bias back to substantially their original position and retain the head portion 110 into the seat. This snap-fit feature can also be accomplished with 3 or more pinch points, as well. In one example, a complete ring comprising infinite pinch points can also be used. A plurality of spaced projections or bumps can also be used.

The receiving element is further adapted to receive a stabilizer rod 500. As such, in one aspect, the receiving element 200 comprises a pair of opposed legs 240 separated by a rod-receiving channel 250. As illustrated in FIG. 9, the rod 500 receiving channel 250 is sized for complementary engagement with a portion of the stabilizer rod. The compression element 400, as discussed below, is configured to work with the receiving element to compress the stabilizer bar onto the coupling element 300. This can be accomplished in several manners, including but not limited to, externally threading the two legs 240 for engagement with an internally threaded nut, or internally threading the two legs for engagement with an externally threaded set screw. As such, in this aspect, the pair of opposed legs 240 defines a compression element receiving chamber 260. In one exemplified aspect, the threads of the opposed legs and complimentary threads of compression element can comprise square threads. As one skilled in the art can appreciate, other thread patterns, such as but not limited to, inwardly tilted threads, dove tail threads, and the like, may be used.

The coupling element is positioned in the receiving element below the stabilizer rod when the stabilizer rod is in the receiving element. In one aspect, a top portion 310 of the coupling element is substantially saddle-shaped to substantially conform to the shape of the stabilizer rod to maximize contact surface area between the coupling element 300 and the stabilizer rod. The coupling element is securable to at least a portion of the head portion of the fixation element 100 and is independent from the receiving element 200. Therefore, when the coupling element is mounted onto the at least a portion of the head portion of the fixation element, the coupling element and the fixation element are coupled together and the coupling of the fixation element and the coupling element 300 permit limited movement in a normal direction of the coupling element relative to the head portion of the fixation element 100. That is, in one aspect, the coupling element snaps onto the head portion 110 of the fixation element such that it does not move off of the head portion, but still permits rotational movement of the head portion of the fixation element with respect to the coupling element.

To accomplish the coupling of the coupling element 300 to the fixation element, in one aspect, the coupling element comprises at least two prongs 320 protruding below a lower portion 330 of the coupling element. The at least two prongs 320 can be configured to be biased from a first relaxed position to a second expanded position. In the first relaxed position, the at least two prongs are spaced a distance less than the maximum diameter of the head portion of the fixation element 100. In the second expanded position, the at least two prongs are spaced at least as much as the maximum diameter $D_M$ of the head portion 110 of the fixation element. In another aspect, each of the at least two prongs 320 comprises a distal engaging portion 322. In this aspect, upon insertion of the coupling element onto a portion of the head portion of the fixation element, the at least two prongs are biased from the first position to the second position until the distal engaging portions 322 pass the point on the head portion of the fixation element where the head portion is at its maximum diameter. At this point, the at least two prongs bias back towards the first relaxed position and the distal engaging portions engage portions of the head portion. This engagement, in this aspect, secures the coupling element 300 onto the head portion of the fixation element 100.

In still another aspect, portions of each of the at least two prongs 320 laterally protrude therefrom a side portion 340 of the coupling element. To accommodate these protrusions, an interior portion 270 of the receiving element defines a slot 280 corresponding to each of the prongs, such that the prongs and the slots are in a mating, but non-engaging relationship. As such, the slots interfere with the prongs 320 to prevent substantial rotational movement of the coupling element about the longitudinal axis $A_L$ of the receiving element. In one aspect, more mass is added during construction to a lower portion of the receiving element to compensate for mass removed by making the slots 280.

The compression element is engagable with the receiving element 200, as discussed herein. In one aspect, the compression element 400 is adapted to move downward into the compression element receiving chamber 260 to translate a force to the stabilizer rod 500 and place it into contact with the coupling element, which translates a force onto the head portion of the fixation element and substantially fixes the position of the fixation element with respect to the receiving element.

Figure 10:
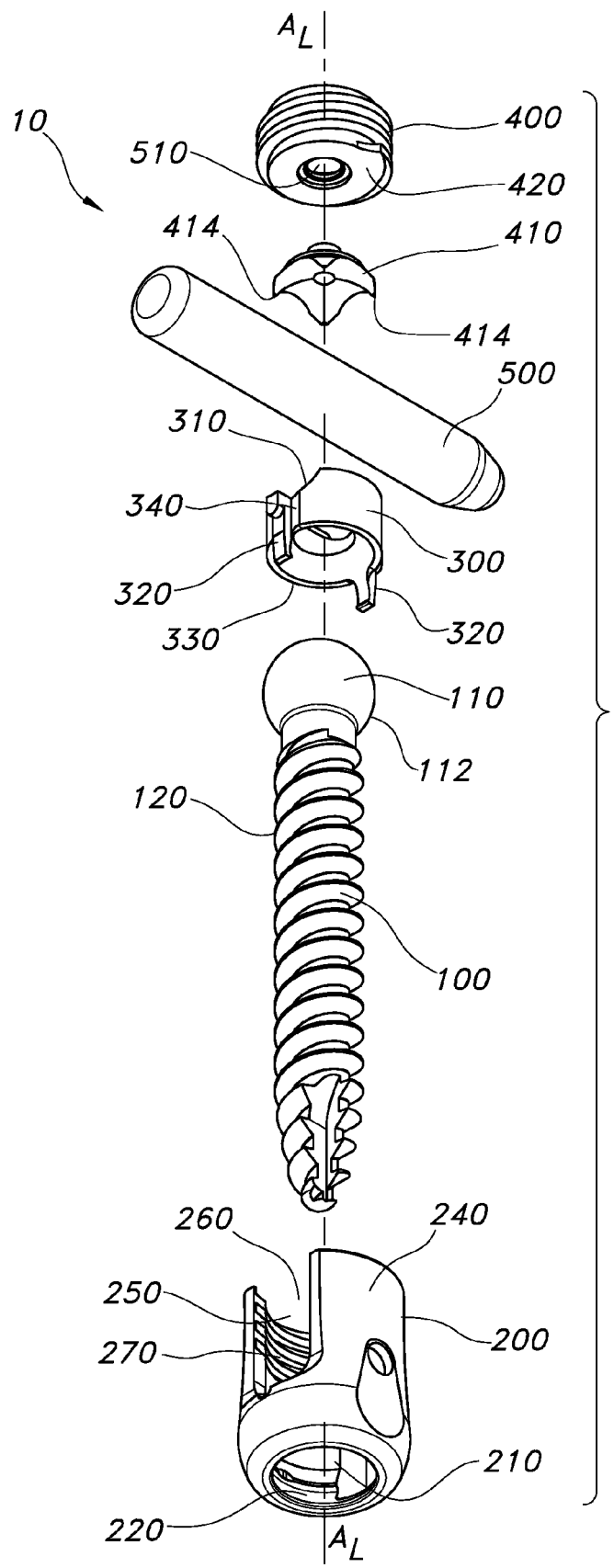
FIG. 10 is an exploded rear perspective view of the bone screw system of FIG. 1.

In still another aspect, the compression element can further comprise a top saddle 410 rotatingly positioned on its bottom face 420. It can, for example, be mounted to the bottom face 420 of the compression element. Alternately, as illustrated in FIG. 9, the top saddle 410 can comprise a male protrusion 412 designed to penetrate the compression element 400 and be retained thereby. In this aspect, the top saddle self-aligns into secure engagement with the stabilizer rod 500 as the top saddle moves downward toward the stabilizer rod. This design maximizes the contact surface area between the compression element 400 and the stabilizer bar. The top saddle 410 shown in FIG. 10 shows a top saddle 410 comprising 4 teeth 414. However, it is contemplated that more or fewer teeth 414 can be used.

The compression element 400 is designed to be driven into the compression element receiving chamber. In one aspect, the top face 430 of the compression element defines a set screw tool bore 440 configured for engagement with an insertion tool. The set screw tool bore 440 can be, but is not necessarily, configured to engage the same insertion tool as the screw tool bore discussed above.

Some practitioners may desire to position the bone screw system with the aid of one or more guide wires. In this case, the practitioner can place a guide wire into the desired target location. In this aspect, the system defines a coaxial aperture along the longitudinal axis $A_L$. Therefore, in this aspect, the compression element 400, the coupling element 300, and the fixation element each define a coaxial guide wire aperture 510. Where there is a top saddle present in the system, the top saddle also defines a coaxial guide wire aperture 510.

As can be appreciated by one skilled in the art, the materials of construction can vary. The materials of construction are generally biocompatible materials for use in surgery. For example, the bone screw system 10 can comprise Titanium or a Titanium alloy, such as Ti 6-4 ELI. The system can also be bead blasted to increase frictional forces and to add stability to the system.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

We claim:

1. A bone screw system, comprising:

a fixation element adapted to engage a bone and having a head portion and a threaded shank portion;

a receiving element having a longitudinal axis and defining an internal bore sized to receive the shank portion of the fixation element and a seat adapted to support the head portion of the fixation element and to retain the head portion of the fixation element within the receiving element while substantially permitting rotational movement of the fixation element with respect to the receiving element, the receiving element further adapted to receive a stabilizer rod wherein the receiving element comprises a pair of opposed legs separated by a rod-receiving channel, the pair of opposed legs defining a compression element receiving chamber, wherein at least two slots are defined adjacent to the rod-receiving channel, wherein the seat of the receiving element is shaped to substantially conform to an exterior portion of the head portion of the fixation element, and wherein the seat of the receiving element further defines at least two opposed pinch points that are spaced less than a maximum diameter of the head portion of the fixation element and can be biased away from each other by compressing the head portion of the fixation element into the seat, whereby, as the portion of the head portion with the maximum diameter passes the pinch points, the pinch points bias back to substantially their original position and retain the head portion into the seat;

a coupling element positioned in the receiving element below the stabilizer rod when the stabilizer rod is in the receiving element and comprising at least two prongs protruding below a lower portion of the coupling element, wherein the at least two prongs are configured to be biased about and between a first relaxed position, and in which the at least two prongs are spaced a distance less than a maximum diameter of the head portion of the fixation element, and a second expanded position in which the at least two prongs are spaced at least as much as the maximum diameter of the head portion of the fixation element, wherein upon insertion of the coupling element onto a portion of the head portion of the fixation element, the at least two prongs are biased from the first position to the second position until the distal engaging portions pass a point on the head portion of the fixation element whereby the portion of the head portion is at its maximum diameter, at which point the at least two prongs bias back towards the first relaxed position and the distal engaging portions engage portions of the head portion to secure the coupling element to the fixation element, wherein a portion of at least one of the at least two prongs protrudes laterally from a side portion of the coupling element, and wherein the at least two slots of the receiving element mates with the portion of the prongs to prevent substantial rotational movement of the coupling element relative to the longitudinal axis of the receiving element; and a compression element engagable with the receiving element, the compression element adapted to move downward into the compression element receiving chamber to translate a force to the stabilizer rod and place it into contact with the coupling element, which translates a force onto the head portion of the fixation element and substantially fixes the position of the fixation element with respect to the receiving element.

2. The bone screw system of claim 1, wherein an inner surface of the opposed legs define inner threads and an outer surface of the compression element define complementary outer threads such that rotation of the compression element drives the compression element into the compression element receiving chamber.

3. The bone screw system of claim 2, wherein the inner threads of the inner surface of the opposed legs and the outer threads of the outer surface of the compression element comprises square threads.

4. The bone screw system of claim 1, wherein the compression element further comprises a top saddle rotatingly positioned on a bottom face of the compression element such that the top saddle self-aligns into secure engagement with the stabilizer rod as the top saddle moves downward toward the stabilizer rod.

5. The bone screw system of claim 4, wherein the compression element, the top saddle, the coupling element, and the fixation element each define a coaxial guide wire aperture.

6. The bone screw system of claim 1, wherein a top portion of the coupling element is substantially saddle-shaped to substantially conform to the shape of the stabilizer rod.

7. The bone screw system of claim 1, wherein the head portion of the fixation element defines a screw tool bore configured for engagement with an insertion tool.

8. The bone screw system of claim 1, wherein the head portion is substantially spherical.

9. The bone screw system of claim 1, wherein a top face of the compression element defines a set screw tool bore configured for engagement with an insertion tool.

10. The bone screw system of claim 1, wherein the compression element, the coupling element, and the fixation element each define a coaxial guide wire aperture.

* * * * *